US00PP18779P3

(12) United States Plant Patent
Meilland

(10) Patent No.: US PP18,779 P3
(45) Date of Patent: Apr. 29, 2008

(54) HYBRID TEA ROSE PLANT NAMED 'MEILABASUN'

(50) Latin Name: *Rosa hybrida*
Varietal Denomination: Meilabasun

(75) Inventor: Alain A. Meilland, Antibes (FR)

(73) Assignee: Meilland International S.A., Le Luc en Provence (FR)

( * ) Notice: Subject to any disclaimer, the term of this patent is extended or adjusted under 35 U.S.C. 154(b) by 0 days.

(21) Appl. No.: 11/481,031

(22) Filed: Jul. 6, 2006

(65) Prior Publication Data

US 2008/0010708 P1 Jan. 10, 2008

(51) Int. Cl.
*A01H 5/00* (2006.01)

(52) U.S. Cl. ..... Plt./130

(58) Field of Classification Search ..... Plt./130, Plt./132, 134
See application file for complete search history.

*Primary Examiner*—Kent Bell
(74) *Attorney, Agent, or Firm*—Buchanan Ingersoll & Rooney PC

(57) ABSTRACT

A new and distinct variety of rose plant of the Hybrid Tea Class is provided which abundantly forms on a nearly continuous basis attractive yellow blossoms that are margined and suffused with red. The growth habit is erect. Attractive dense dark green and glossy foliage is formed that contrasts nicely with the blossoms coloration. Tolerance to disease is good particularly with respect to Oidium and Botrytis. The new variety forces well under greenhouse growing conditions and is well suited for cut flower production under such conditions.

1 Drawing Sheet

Botanical/commercial classification: *Rosa hybrida*/Hybrid Tea Rose Plant.
Varietal denomination: cv. 'Meilabasun'.

SUMMARY OF THE INVENTION

The new variety of Hybrid Tea rose plant was discovered at Le Cannet des Maures, Var, France, while growing among a group of plants of the 'Meilambra' variety (non-patented in the United States). The plant displayed distinctive yellow flowers that are margined and suffused with red unlike those of its parent, and is considered to be a mutation of unknown causation of the 'Meilambra' variety. Had the plant of the new variety not been discovered, preserved, and subsequently studied to confirm its characteristics, it would have been lost to mankind.

It was found that the Hybrid Tea rose plant of the present invention possesses the following combination of characteristics:

(a) exhibits an erect growth habit,
(b) forms in abundance on a nearly continuous basis attractive yellow blossoms that are margined and suffused with red,
(c) forms attractive dense dark green and glossy foliage that contrasts well with the blossom coloration, and
(d) is particularly well suited for cut flower production under greenhouse growing conditions.

The tolerance to disease is very good particularly with respect to Oidium and Botrytis.

The new variety of the present invention can be readily distinguished from its parental 'Meliambra' variety. More specifically, the 'Meilambra' variety forms bicolored blossoms that are red on the upper surface and yellow on the under surface of the petals.

The new variety performs well under greenhouse growing conditions while producing cut flowers.

The new variety has been found to undergo asexual propagation in France by a number of routes, including budding, grafting, and cuttage. Asexual propagation by the above-mentioned techniques in France has confirmed that the characteristics of the new variety are stable and are strictly transmissible by such asexual propagation from one generation to another.

The new variety has been named the 'Meilabasun'.

BRIEF DESCRIPTION OF THE PHOTOGRAPH

The accompanying photograph shows as nearly true as it is reasonably possible to make the same, in a color illustration of this character, a typical specimen of the new variety. The rose plant of the new variety was one year of age and was observed during June while budded on *Rosa indica major* understock and growing under greenhouse conditions at Le Cannet des Maures, Var, France. Elegant blossoms in various stages of opening as well as the dark green and glossy foliage are shown.

DETAILED DESCRIPTION

The chart used in the identification of the colors is that of The Royal Horticultural Society (R.H.S. Colour Chart). The description is based on the observation of one-year-old plants during June while budded on *Rosa indica major* understock and growing under greenhouse conditions at Le Cannet des Maures, Var, France.

Class: Hybrid Tea.
Plant:

*Height.*—When pruned to a height of 85 cm, floral stems having lengths of approximately 70 to 80 cm commonly are produced. A typical plant height is approximately 170 cm.

*Width.*—A typical plant width has not been determined since the erect plant is primarily grown in greenhouses for cut flower production.

*Habit.*—Erect.

Branches:

*Color.*—Young stems: near Green Group 137A and 137B. Adult wood: near Green Group 137B and 137C.

*Thorns.*—Configuration: rather longish pointed, curved downwards on the upper surface, and concave on the under surface. Size: approximately 0.5 cm in length on average with an ovate base on young stems, and approximately 0.9 cm in length on average with an ovate base on adult stems. Quantity: approximately 4 on average over a young stem length of 15 cm, and approximately 10 on average over an adult stem length of 15 cm. Color: near Green Group 143C on young stems, and near Green Group 143C on adult stems.

*Prickles.*—Size: approximately 0.2 cm in length on average with an ovate base on young stems, and approximately 0.4 cm in length on average with an ovate base on adult stems. Quantity: approximately 10 on average over a stem length of 15 cm on young stems, and approximately 7 on average over a stem length of 15 cm on adult stems. Color: near Green Group 143C on young stems, and near Green Group 143C on adult stems.

Leaves:

*Stipules.*—Smooth, adnate, pectinate, broad, approximately 2 cm in length on average, approximately 0.3 cm in width on average, near Yellow-Green Group 147A on the upper surface, and near Yellow-Green Group 147B on the under surface.

*Petioles.*—Upper surface: near Green-Group 137A and 137B. Under surface: near Green-Group 137A and 137B. Length: approximately 3.4 cm on average. Diameter: Approximately 0.2 cm on average.

*Rachis.*—Upper surface: near Green Group 137A and 137B. Under surface: near Green Group 137A and 137B. Length: approximately 5.4 cm on average. Diameter: approximately 0.1 cm on average.

*Leaflets.*—Number: 3, 5 (most often), and 7. Shape: ovate with a symmetrical tip and a cordate base. Apex: sometimes slightly cuspidate and symmetrical. Serration: single and fine (as illustrated). Texture: firm, and glossy. General appearance: dense and dark green. Size: terminal leaflets commonly measure approximately 7.2 cm in length, and approximately 5.3 cm in width. Color (young foliage): Upper surface: near Green Group 139A. Under surface: near Yellow-Green Group 147B. Color (adult foliage): Upper surface: near Yellow-Green Group 147A. Under surface: near Yellow Green Group 147B.

Inflorescence:

*Number of flowers.*—Commonly one flower per stem.

*Peduncle.*—Smooth, year Yellow-Green Group 144A in coloration, approximately 2.5 cm in length on average, and approximately 0.5 cm in diameter on average.

*Sepals.*—Upper surface: tomentose, and near Yellow-Green Group 144B in coloration. Under surface: tomentose, and near Yellow-Green Group 144A in coloration. Length: approximately 3 cm on average. Width: approximately 1.5 cm on average. Shape: longish pointed and narrow with a straight base. Extensions: commonly three sepals possess very weak extensions and two sepals commonly possess no extensions.

*Buds.*—Shape: conical. Size: medium. Length: approximately 5 cm on average. Width: approximately 2.8 cm on average. Color as the calyx breaks: Upper surface: near Yellow Group 7A and amply margined and suffused with Red Group 46B. Under surface: near Yellow Group 6A margined with Red Group 46A.

*Flower.*—Shape: high-pointed, and during opening the central petals assume a somewhat pointed configuration and extend above the outer petals. Diameter: approximately 12 cm on average when open. Color (in the course of opening): Upper surface: near Yellow Group 7A margined with Red Group 46C. Under surface: near Yellow Group 8C, amply suffused with Yellow Group 8A, and slightly margined with Red Group 45D. Basal color spot: none. Color (when open): Upper surface: near Yellow Group 4D, amply margined with Red Group 53C and 53D and slightly suffused with Red Group 53D. Under surface: near Yellow Group 4D, suffused with Yellow Group 3D, and slightly margined with Red Group 53D. Basal color spot: near Yellow Group 8A on upper surface only. Lasting quality: very long and commonly approximately 15 days on average on the plant and approximately 12 days on average when out and placed in a vase. Petal number: commonly approximately 25 on average under normal growing conditions. Petal arrangement: imbricated. Petaloids: none observed. Petal shape: oval, broader than length, flattened rounded base, rounded reflexed tip, approximately 4.3 cm in length on average, and approximately 6 cm in width on average. Petal margin: entire, slightly ruffled, and soft. Petal texture: consistent. Petal drop: good, the petals commonly detach cleanly before drying. Fragrance: none. Stamen number: approximately 170 on average. Anthers: near Yellow-Orange Group 18A in coloration, approximately 3 mm in length, and regularly arranged around the styles. Filaments: near Yellow Group 12A in coloration, and approximately 0.4 cm in length. Pistils: approximately 110 on average. Stigmas: near Yellow-Orange Group 15D in coloration, and approximately 0.1 cm in size on average. Styles: near Yellow Group 12C and 12D in coloration, and the length is approximately 0.5 cm on average. Receptacle: Shape: pitched-shaped in longitudinal section. Length: approximately 1 cm on average. Width: approximately 1 cm on average. Texture: smooth. Color: near Yellow-Green Group 144A. Hips: none observed to date under greenhouse growing conditions.

Development:

*Vegetation.*—Strong.

*Blooming.*—Early, abundant and nearly continuous.

*Tolerance to diseases.*—Very good with respect to Oidium and Botrytis.

*Aptitude to forcing.*—Very good.

I claim:

1. A new and distinct Hybrid Tea rose plant which exhibits the following combination of characteristics:

(a) exhibits an erect growth habit, (b) forms in abundance on a nearly continuous basis attractive yellow blossoms that are margined and suffused with red, (c) forms attractive dense dark green and glossy foliage that contrasts well with the blossoms coloration, and (d) is particularly well suited for cut flower production under greenhouse growing conditions;

substantially as illustrated and described.

* * * * *

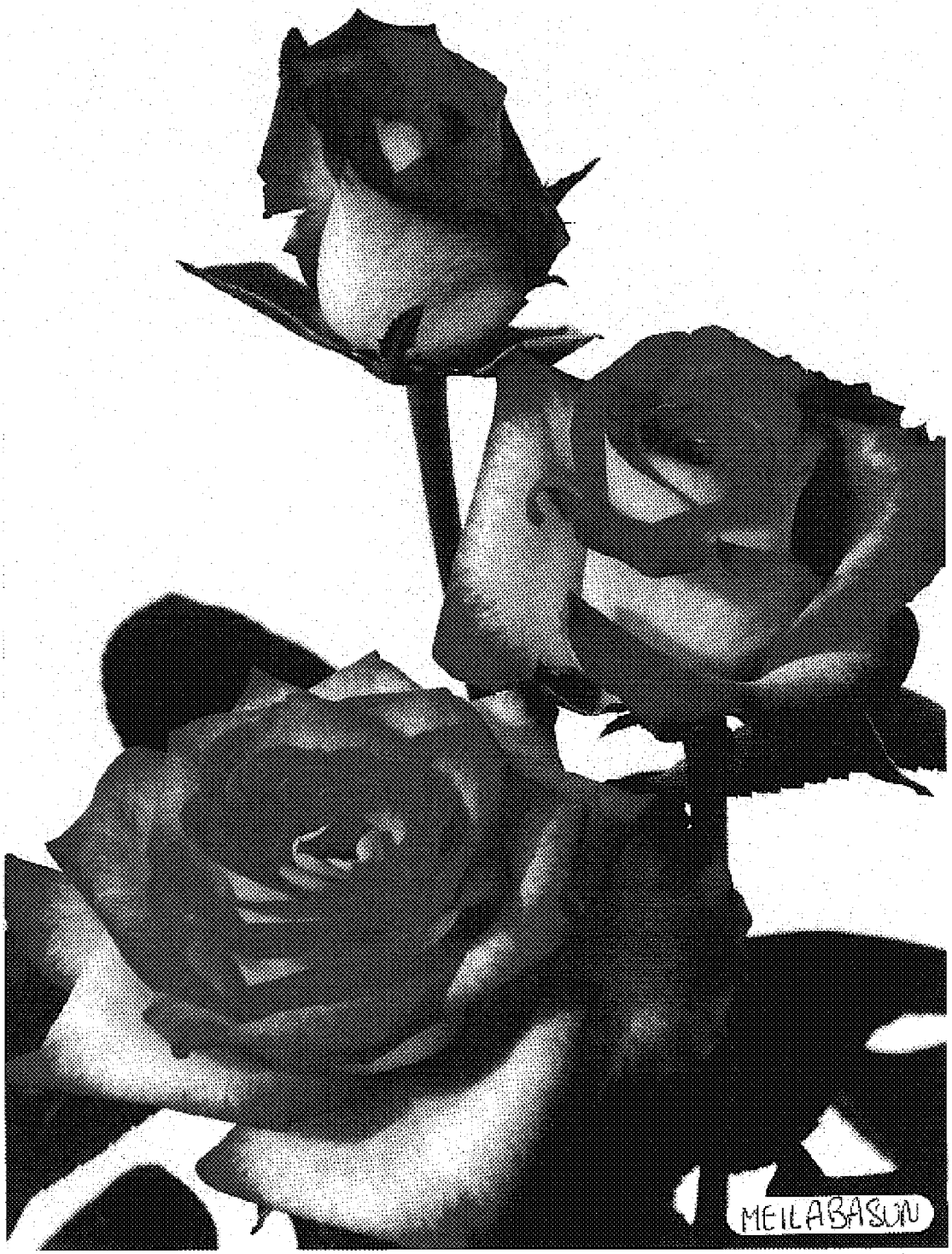
MEILABASON